(12) United States Patent
Hao et al.

(10) Patent No.: US 9,222,860 B2
(45) Date of Patent: Dec. 29, 2015

(54) TAPPING HAMMER FOR TAPPING TEST

(71) Applicants: BOE Technology Group Co., Ltd., Beijing (CN); Beijing BOE Display Technology Co., Ltd., Beijing (CN)

(72) Inventors: Zhibin Hao, Beijing (CN); Huanyu Guo, Beijing (CN)

(73) Assignees: BOE Technology Group Co., Ltd., Beijing (CN); Beijing BOE Display Technology Co., Ltd., Beijing (CN)

( * ) Notice: Subject to any disclaimer, the term of this patent is extended or adjusted under 35 U.S.C. 154(b) by 107 days.

(21) Appl. No.: 14/094,999

(22) Filed: Dec. 3, 2013

(65) Prior Publication Data

US 2014/0165696 A1    Jun. 19, 2014

(30) Foreign Application Priority Data

Dec. 14, 2012   (CN) .......................... 2012 1 0546056

(51) Int. Cl.
| | |
|---|---|
| *G01M 7/00* | (2006.01) |
| *G01N 3/00* | (2006.01) |
| *G01N 33/00* | (2006.01) |
| *G01P 15/00* | (2006.01) |
| *G01N 3/02* | (2006.01) |
| *G01N 3/30* | (2006.01) |
| *G01M 7/08* | (2006.01) |

(52) U.S. Cl.
CPC . *G01N 3/02* (2013.01); *G01M 7/08* (2013.01); *G01N 3/30* (2013.01); *G01N 2203/0039* (2013.01)

(58) Field of Classification Search
CPC .. G01N 3/02; G01N 3/066; G01N 2203/0039
USPC ........................................................ 73/12.09
See application file for complete search history.

(56) References Cited

U.S. PATENT DOCUMENTS

| | | | |
|---|---|---|---|
| 4,225,802 A | | 9/1980 | Suzuki et al. |
| 4,799,375 A | * | 1/1989 | Lally ............................ 73/12.09 |
| 5,025,655 A | * | 6/1991 | Umemura et al. ........... 73/12.09 |

(Continued)

FOREIGN PATENT DOCUMENTS

CN          101655534 A       2/2010

OTHER PUBLICATIONS

Article from China Academic Journal Electronic Publishing House, numbered 950359, pp. 1-13 in Chinese with English abstract, date submitted to publisher: Jun. 25, 1984.

*Primary Examiner* — Lisa Caputo
*Assistant Examiner* — Roger Hernandez-Prewitt
(74) *Attorney, Agent, or Firm* — Frommer Lawrence & Haug LLP

(57) ABSTRACT

The present invention provides a tapping hammer for tapping test, which can help a user to accurately control the tapping force during a tapping test. The tapping hammer comprises a hammerhead and a handle supporting the hammerhead, and further comprises an alarm, a power source and a conductor, a hollowed-out region is provided in the interior of the hammerhead, the hammerhead is elastically deformable and electrically connected to a first electrode of the power source; the conductor is fixed in the interior hollowed-out region, not electrically connected to the hammerhead while no tapping force is exerted on the hammerhead and electrically connected to the hammerhead while a tapping force larger than a certain amount is exerted on the hammerhead; a first electrode of the alarm is connected to the conductor, a second electrode of the alarm is connected to a second electrode of the power source.

19 Claims, 5 Drawing Sheets

(56) References Cited

U.S. PATENT DOCUMENTS

| | | | |
|---|---|---|---|
| 5,657,763 A * | 8/1997 | Schneider | 600/553 |
| 5,895,840 A | 4/1999 | Ohuchi et al. | |
| 2005/0037862 A1* | 2/2005 | Hagood et al. | 473/345 |
| 2013/0073246 A1* | 3/2013 | Sprague | 702/140 |

* cited by examiner

US 9,222,860 B2

TAPPING HAMMER FOR TAPPING TEST

FIELD OF THE INVENTION

The present invention relates to the field of display manufacturing technologies, more particularly, to a tapping hammer for tapping test.

BACKGROUND OF THE INVENTION

While testing a display product, a tapping hammer is required to be used in a tapping test to check the bonding effect, e.g., the bonding effect between a finished Printed Circuit Board Assembly (PCBA) and outer leads of a Chip on Film (COF). Whether a bonding is successful is checked through the tapping test. For example, if bright lines appear in a screen during tapping, the bonding is determined to be faulty. Here, PCBA refers to the whole process of mounting devices via Surface Mounted Technology (SMT) and then plugging devices on a blank PCB.

However, as a user cannot determine the required tapping force during the tapping test, products can easily get damaged during the tapping test.

SUMMARY OF THE INVENTION

The present invention provides a tapping hammer for tapping test, which may help a user to control the tapping force during the tapping test, thereby reducing damage rate of products during the tapping test.

To achieve the above objective, the present invention provides the following technical solutions.

The present invention provides a tapping hammer for tapping test, comprising a hammerhead and a handle supporting the hammerhead, characterized in that, the tapping hammer further comprises an alarm, a power source and a conductor, wherein a hollowed-out region is provided in the interior of the hammerhead, the hammerhead is elastically deformable, and the hammerhead is electrically connected to a first electrode of the power source; the conductor is fixed in the interior hollowed-out region of the hammerhead, the conductor is not electrically connected to the hammerhead while no tapping force is exerted on the hammerhead, and the conductor is electrically connected to the hammerhead while a tapping force larger than a certain amount is exerted on the hammerhead; a first electrode of the alarm is connected to the conductor, a second electrode of the alarm is connected to a second electrode of the power source.

The present invention controls whether the alarm raises an alarm by controlling whether the conductor is electrically connected to the inner surface of the hammerhead, thereby helping the user to control the tapping force during the tapping test, so as to reduce damage rate of products during the tapping test.

BRIEF DESCRIPTION OF THE DRAWINGS

In order to clearly illustrate the technical solutions of the present invention or the prior art, the drawings of the embodiments or the prior art will be briefly described in the following. It is obvious that the described drawings are only related to some embodiments of the present invention and the person skilled in the art may arrive at other drawings based on these drawings without creative efforts. In the drawings.

DETAILED DESCRIPTION OF EMBODIMENTS

Figure 1A:
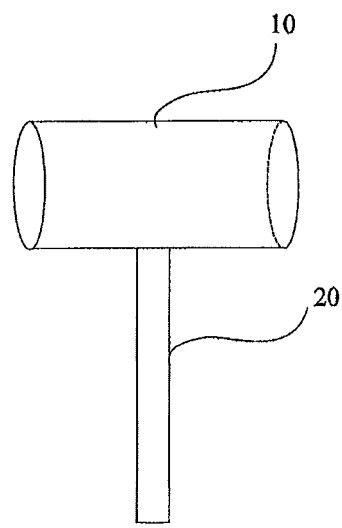
FIG. 1A is a schematic side view of a structure of a tapping hammer as provided by Embodiment 1 of the present invention.

The technical solutions of the embodiments will be described clearly and completely in connection with the drawings. Obviously, the described embodiments are only a part but not all of the embodiments of the present invention. Based on the described embodiments, other embodiment(s) obtained by the person skilled in the art without creative efforts, should be within the protection scope of the present invention.

Embodiments of the present invention provide tapping hammers 1 for tapping test, as illustrated in FIGS. 1 to 8. The tapping hammer 1 comprises a hammerhead 10 and a handle 20 supporting the hammerhead 10. Further, the tapping hammer 1 also comprises an alarm 90, a power source 80 and a conductor 30, wherein, a hollowed-out region is provided in the interior of the hammerhead 10, the hammerhead 10 is elastically deformable, and the hammerhead 10 is electrically connected to a first electrode 81 of the power source 80; the conductor 30 is fixed in the interior hollowed-out region of the hammerhead 10, the conductor 30 is not electrically connected to the hammerhead 10 while no tapping force is exerted on the hammerhead 10, and the conductor 30 is electrically connected to the hammerhead 10 while a tapping force larger than a certain amount is exerted on the hammerhead 10; a first electrode 91 of the alarm 90 is electrically connected to the conductor 30, a second electrode 92 of the alarm 90 is electrically connected to a second electrode 82 of the power source 80.

For example, in a case where the first electrode is an anode and the second electrode is a cathode, the working principle of the tapping hammer 1 is as follows: the hammerhead 10 is electrically connected to the anode of the power source, the cathode of the alarm is electrically connected to the cathode of the power source, the anode of the alarm is electrically connected to the conductor 30; the conductor 30 is not electrically connected to the hammerhead 10 while no tapping force is exerted on the hammerhead 10, and the conductor 30 is electrically connected to the inner surface of the hammerhead 10 while a tapping force larger than a certain amount is exerted on the hammerhead 10. Thus, the tapping hammer 1 is designed for determining different tapping forces according to whether the alarm raises an alarm while no tapping force or a tapping force larger than the certain amount is exerted on the hammerhead 10, which helps the user to control the tapping force while using the tapping hammer 1.

The followings should be noted: firstly, the conductor 30 and the handle 20 may be integrated or separated, which will not be limited here; secondly, a hollowed-out region is provided in the interior of the hammerhead 10, that is, a part of the interior region of the hammerhead 10 is hollowed out, or the hammerhead 10 is of a hollow structure; thirdly, the first electrode of the power source can be an anode or a cathode, accordingly, the second electrode of the power source can be a cathode or an anode, as long as one of the first and second electrodes is an anode and the other is a cathode, which also applies to the first and second electrodes of the alarm, and will not be redundantly described here; fourthly, the structure of the handle 20 will not be limited, and preferably, the handle 20 is a cylinder. In addition, positions where the power source and the alarm are provided will not be limited in the embodiments of the present invention. In specific applications, the alarm may be a device that can effectively show the tapping force or raise an alarm according to the tapping force, such as a buzzer or a pressure display.

The present invention controls whether the alarm raises an alarm by controlling whether the conductor is electrically connected to the inner surface of the hammerhead, thereby helping the user to accurately control the tapping force, such that the damage rate of the products during the tapping test may be reduced.

Embodiment 1

Figure 1B:
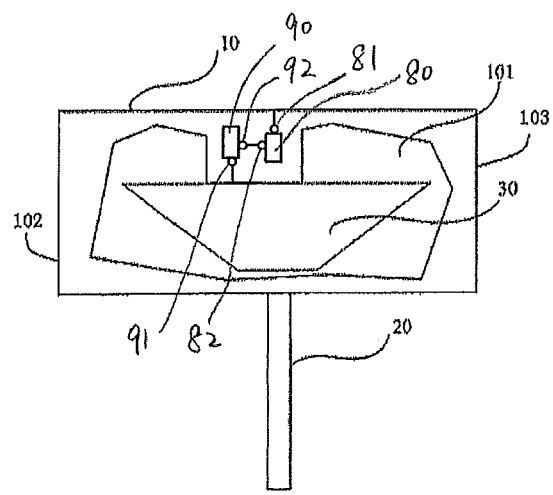
FIG. 1B is a schematic cutaway view of the structure of the tapping hammer of FIG. 1A.

FIGS. 1A and 1B are a side view and a cutaway view of a tapping hammer 1, respectively. As illustrated in FIG. 1A, the hammerhead 10 is a cylinder, and as illustrated in FIG. 1B, a hollowed-out region 101, which may be an irregular shape, is provided in the interior of the hammerhead 10. The conductor 30 is fixed in the hollowed-out region 101 by any means, as long as the conductor 30 is not electrically connected to the hammerhead 10 while no tapping force is exerted on the hammerhead 10. In this embodiment, for example, a protrusion may be provided on the inner surface of the hammerhead 10, an insulator is provided between the protrusion and the conductor 30, and the protrusion, the insulator and the conductor 30 are connected, such that the conductor 30 is fixed in the interior hollowed-out region 101 of the hammerhead 10.

In this embodiment, the conductor 30 is, for example, a truncated cone whose upper base (the base with a larger area) is fixed to a side of the inner surface of the hammerhead 10 farther away from the handle 20 via the insulator, and whose lower base (the base with a smaller area) is provided close to the handle 20 but not in contact with the inner surface of the hammerhead 10. Here, assuming that stress surfaces of the hammerhead 10 are the two bases 102 and 103 of the cylinder, the shortest distances between an edge where the lateral surface of the truncated conical conductor 30 joins the upper base of the truncated conical conductor 30 and inner surfaces of the two bases 102 and 103 of the hammerhead 10 are a first distance and a second distance. Here, the first distance and the second distance are distances corresponding to the tapping force obtained according to the elastic material of the hammerhead 10 and experiences. For example, in case that the first distance is 2 cm, the alarm raises an alarm under a tapping force of 5 Newton. Furthermore, if the tapping hammer 1 is expected to raise an alarm under a tapping force of 10 Newton, the second distance can be set to be a distance for the alarm to raise an alarm under the tapping force of 10 Newton, for example, 4 cm.

It should be noted that shapes of the hollowed-out region 101 and the conductor 30 will not be limited in the embodiment, as long as the inner surface of the hammerhead 10 contacts the conductor 30 under a tapping force larger than a certain amount such that the alarm may raise an alarm. The manner in which the conductor 30 is fixed is not limited here, as long as the alarm may raise an alarm while a tapping force larger than a certain amount is exerted on the stress surfaces of the tapping hammer 1. Furthermore, the relationship between the first distance and the tapping force are only illustrative for clarity of description, and the actual relationship should be obtained according to the material and thickness of the hammerhead 10 and the position and structure of the conductor 30, which will not be redundantly described here.

Embodiment 2

Figure 2:
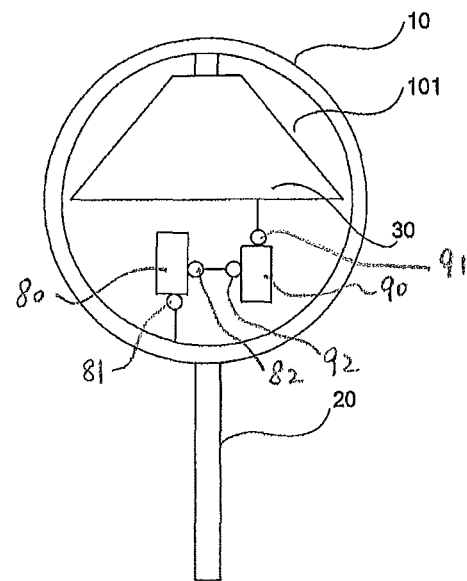
FIG. 2 is a schematic cutaway view of a structure of a tapping hammer as provided by Embodiment 2 of the present invention.
Figure 3:
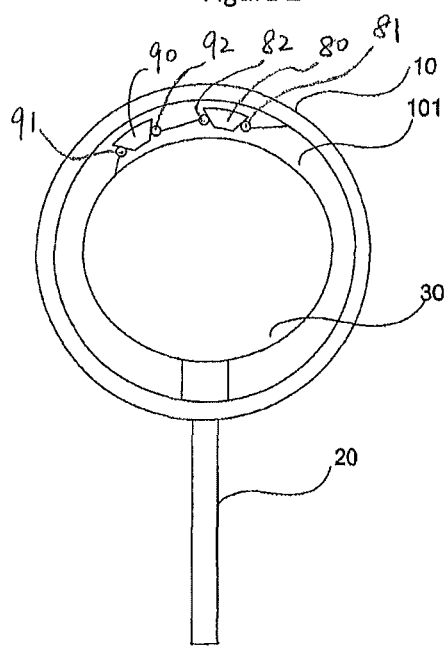
FIG. 3 is a schematic cutaway view of a structure of another tapping hammer as provided by Embodiment 2 of the present invention.

FIGS. 2 and 3 are cutaway views of another tapping hammer 1, respectively. As illustrated in FIGS. 2 and 3, the hammerhead 10 is a sphere whose interior is a hollow structure, that is, a hollowed-out region 101 is provided in the interior of the hammerhead 10. A thickness between the inner surface and the outer surface of the hammerhead 10 is constant and the thickness of the hammerhead 10 may be made quite thin as required, which will not be limited here. A non-conductive protrusion is provided on the inner surface of the hammerhead 10, and the conductor 30 may be fixed inside the hollowed-out region 101 of the hammerhead 10 through the non-conductive protrusion.

As illustrated in FIG. 2, the conductor 30 may be, for example, a truncated cone whose upper base (the base with a smaller area) is fixed to a side of the inner surface of the hammerhead 10 farther away from the handle 20 through the non-conductive protrusion on the inner surface of the hammerhead 10, of course, the upper base can also be fixed to a side of the inner surface of the hammerhead 10 closer to the handle 20. A lower base (the base with a larger area) of the conductor 30 is provided close to the handle 20 but kept a distance from the inner surface of the hammerhead 10. For example, a distance corresponding to a tapping force may be obtained empirically according to the elastic material and the thickness of the hammerhead 10, such that the tapping force for triggering the alarm to raise an alarm may be determined.

As illustrated in FIG. 3, the conductor 30 may be, for example, a sphere, which may be fixed on an inner surface corresponding to non-stress surface of the hammerhead 10 via the non-conductive protrusion on the inner surface of the hammerhead 10. Similar to the above FIG. 2, the distance between the spherical conductor 30 and the inner surface of the hammerhead 10 may be controlled to control the tapping force for triggering the alarm to raise an alarm, which will not be redundantly described here.

Further, the tapping hammer 1 also comprises at least one first spring 40 and at least one second spring 50. Both ends of each first spring 40 are connected to the conductor 30 and the inner surface of the hammerhead 10, respectively, and the at least one first spring 40 is non-conductive. Both ends of each second spring 50 are fixed to a same first spring 40, and wherein, one end of each second spring 50 is electrically connected to the conductor 30 or the inner surface of the hammerhead 10. In a case where one end of the second spring 50 is electrically connected to the conductor 30, the other end of the second spring 50 is not electrically connected to the inner surface of the hammerhead 10 while no tapping force is exerted on the hammerhead 10, and is electrically connected to the inner surface of the hammerhead 10 while a tapping force larger than a certain amount is exerted on the hammerhead 10. In a case where one end of the second spring 50 is electrically connected to the inner surface of the hammerhead 10, the other end of the second spring 50 is not electrically connected to the conductor 30 while no tapping force is exerted on the hammerhead 10, and is electrically connected to the conductor 30 while a tapping force larger than a certain amount is exerted on the hammerhead 10.

Embodiment 3

Figure 4:
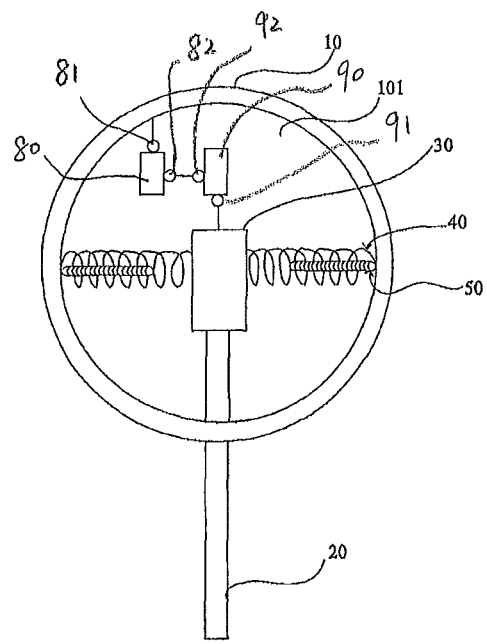
FIG. 4 is a schematic cutaway view of a structure of a tapping hammer as provided by Embodiment 3 of the present invention.

FIG. 4 is a cutaway view of a tapping hammer 1. As illustrated in FIG. 4, the tapping hammer 1 comprises a spherical hammerhead 10, a cylindrical handle 20, a cylindrical conductor 30 located in the interior hollowed-out region 101 of the hammerhead 10, at least one first spring 40 (two first springs 40 are illustrated in FIG. 4) and at least one second spring 50 (two second springs 50 are illustrated in FIG. 4), wherein both ends of each first spring 40 are connected to the inner surface of the hammerhead 10 and the conductor 30, respectively, and the first springs 40 are non-conductive. Both ends of each second spring 50 are fixed to a same first spring 40, and one end of each second spring 50 is electrically connected to the inner surface of the hammerhead 10 (or the conductor 30), that is, the second springs 50 are conductive. Further, the tapping hammer 1 also comprises a power source (not shown in Figures), an alarm (not shown in Figures), wherein, a first electrode of the power source (e.g. the anode) is electrically connected to the hammerhead 10, a second electrode of the power source (e.g. the cathode) is electrically connected to a second electrode of the alarm (e.g. the cathode), and a first electrode of the alarm (e.g. the anode) is electrically connected to the conductor.

Wherein, a protrusion may be provided on the inner surface of the hammerhead 10, such that one end of the first spring 40 is connected to the protrusion on the inner surface of the hammerhead 10. Similarly, a protrusion may also be provided on the conductor 30, such that the other end of the first spring 40 is connected to the protrusion on the conductor 30.

In case that a tapping force larger than a certain amount is exerted on a side of the hammerhead 10 to which the second spring 50 is fixed, one end of the second spring 50 is in contact with and electrically connected to the conductor 30. As the other end of the second spring 50 has already been electrically connected to the inner surface of the hammerhead 1, the alarm thus raises an alarm. Wherein, a length of the second spring 50 may be set as required, that is, in case that one end of the second spring 50 contacts the inner surface of the hammerhead 10, a distance between the other end of the second spring 50 and the conductor 30 may be adjusted. Alternatively, in case that one end of the second spring 50 contacts the conductor 30, a distance between the other end of the second spring 50 and the inner surface of the hammerhead 10 may be adjusted, such that the tapping force for triggering the alarm to raise an alarm is adjusted.

It should be noted that this embodiment is described with reference to the example with the spherical hammerhead 10 which is a hollow structure, however, the embodiments of the present invention is not limited thereto. Moreover, the thickness of the hammerhead 10 may be set according to practical requirements. As to the first spring 40, considering the characteristics of the spherical shape, it is preferably provided on a plane perpendicular to the handle 20 and comprising the sphere center of the spherical hammerhead in case of being used in conjunction with the spherical hammerhead 10.

Further, the conductor 30 may be coaxially provided with the handle 20, and the position of the conductor 30 in the interior hollowed-out region 101 of the hammerhead 10 is adjustable along the axis.

Embodiment 4

Figure 5A:
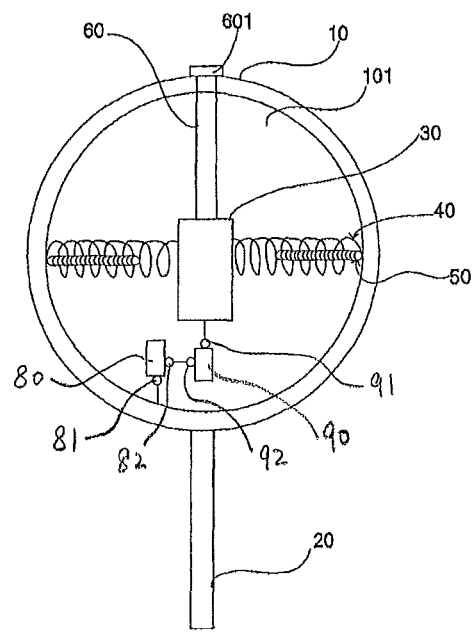
FIG. 5A is a first schematic cutaway view of a structure of a tapping hammer as provided by Embodiment 4 of the present invention.

As described above, the tapping force for triggering the alarm to raise an alarm can be adjusted by, for example, adjusting the distance between one end of the second spring 50 and the conductor 30. As illustrated in FIG. 5A, a non-conductive fixing rod 60 may be provided, on one hand, one end of the fixing rod 60 may be fixed to the conductor 30 in the hollowed-out region 101, on the other hand, the other end of the fixing rod 60 may extend out of the hammerhead 10, and the fixing rod 60 is fixed by a fixing member 601 such as a bayonet, such that the conductor 30 cannot be moved while the tapping hammer 10 is being tapped, wherein the fixing rod 60 and/or the fixing member 601 are non-conductive.

Figure 5B:
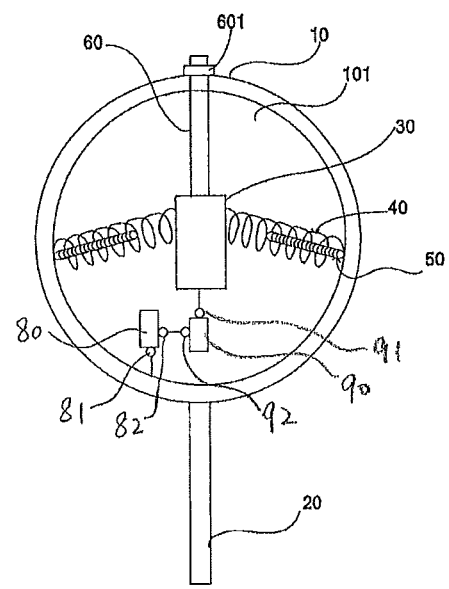
FIG. 5B is a second schematic cutaway view of the structure of the tapping hammer of FIG. 5A.

In case that it needs to increase the tapping force for triggering the alarm of the tapping hammer 1 to raise an alarm, the fixing member 601 may be not fixed, such that the fixing rod 60 may be pulled upwards (that is, in a direction farther away from the center of the hammerhead 10), and the fixing member 601 is fixed again in case that the fixing rod 60 reach a certain location, as illustrated in FIG. 5B. In case that the conductor 30 is moved upwards (that is, in a direction farther away from the center of the hammerhead 10), the first spring 40 is thus deformed, that is, the length of the first spring 40 is elongated, and its elasticity is accordingly increased, such that the distance between the second spring 50 and the conductor 30 is increased, and the tapping force for triggering the alarm of the tapping hammer 1 to raise an alarm is increased as well.

Further, a guide rail may be provided on the conductor 30. One end of the first spring 40 is fixed in the guide rail of the conductor 30 and is slidable along the guide rail, and the other end of the first spring 40 is fixed on the inner surface of the hammerhead 10, wherein the extending direction of the guide rail is perpendicular to the axis of the conductor 30.

Here, a case where the conductor 30 may be rotated and moved in the direction of its axis will be considered. In this case, if the first spring 40 is immovably fixed to the conductor 30 without sliding, the end of the first spring 40 that contacts the conductor 30 will be rotated along with the rotation of the conductor 30, causing the first spring 40 to be tangled, which will damage the first and the second springs 40 and 50. As a result, even if a tapping force large enough to trigger the alarm to raise an alarm is exerted on the tapping hammer 1, the alarm of the tapping hammer 1 may not raise an alarm.

Therefore, in this embodiment, the guide rail is provided on a part of the outer surface of the conductor 30, and one end of the first spring 40 is fixed in the guide rail on the conductor 30. As such, in case that the conductor 30 is moved in the direction of its axis and is rotated, the end of the first spring 40 that contacts the conductor 30 is only moved along the axis direction of the conductor 30, thereby avoiding the damage of the first spring 40 caused by the movement of the end of the first spring 40 that contacts the conductor 30 along a direction perpendicular to the axis of the conductor 30. In this embodiment, an example with two first springs 40 is illustrated.

According to the above description, the tapping hammer 1 according to the embodiment of the present invention may change the tapping force for triggering the alarm to raise an alarm by adjusting the position of the conductor 30, thereby helping the user to accurately control the tapping force according to test requirements for different products and to reduce damage rate of products during the tapping test.

Optionally, the tapping hammer 1 further comprises a screw nut 70, the conductor 30 passes through the hammerhead 10 and extends out of the hammerhead 10, and is fixed to the handle 20; the screw nut 70 is embedded between the hammerhead 10 and the conductor 30, the conductor 30 passes through the screw nut 70, and screw threads matching the screw nut 70 are provided on a part of the outer surface of the conductor 30.

Embodiment 5

Figure 6:
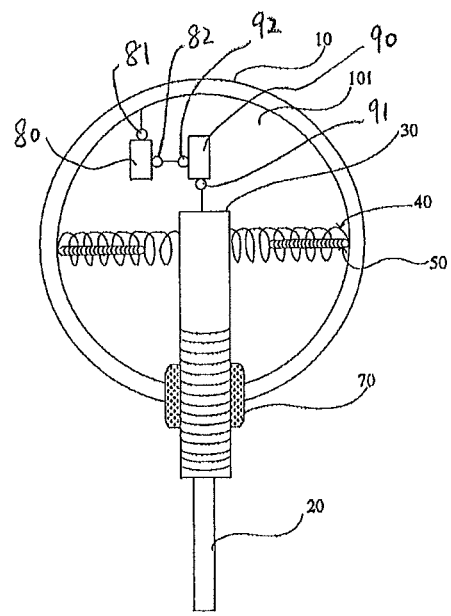
FIG. 6 is a schematic cutaway view of a structure of a tapping hammer as provided by Embodiment 5 of the present invention.

As illustrated in FIG. 6, the conductor 30 and the handle 20 may be integrally fixed together. To adjust the position of the conductor 30 in the interior hollowed-out region 101 of the hammerhead 10 along the axial direction of the conductor 30, the conductor 30 may pass through the hammerhead 10 and extend out of the hammerhead 10, and be fixed to the handle 20. The conductor 30 is fixed by embedding the screw nut 70 between the hammerhead 10 and the conductor 30 and the handle 20 is fixed as well, wherein the screw nut 70 is made of a non-conductive material. As such, in case that the conductor 30 passes through the screw nut 70, it can be ensured that the conductor 30 is not electrically connected with the hammerhead 10 while no tapping force is exerted on the hammerhead 10.

Moreover, considering the characteristics of the screw nut 70, screw threads are required to be provided on a part of the outer surface of the conductor 30 to match the screw nut 70, thereby securing the conductor 30 and the handle 20. The position of the conductor 30 in the interior hollowed-out region 101 of the hammerhead 10 may be adjusted by rotating the handle 20 and the conductor 30.

In case that it needs to adjust the tapping force for triggering the alarm to raise an alarm, that is, to adjust the position of the conductor 30 in the interior hollowed-out region 101 of the hammerhead 10, the conductor 30 can be moved along its axial direction by rotating the handle 20 and the conductor 30.

Furthermore, scale numbers may be marked on the screw threads on the outer surface of the conductor 30. By this means, in case that a scale number is aligned to an end of the screw nut (e.g., the end exposed outside the hammerhead 10), the user can know the currently required tapping force for triggering the alarm of the tapping hammer to raise an alarm, which helps the user to accurately control the tapping force.

Optionally, the handle 20 may pass through the hammerhead 10 and extend into the interior hollowed-out region 101 of the hammerhead 10, and be fixed to the conductor 30. Now, the screw nut 70 is embedded between the hammerhead 10 and the handle 20, the handle 20 passes through the screw nut 70, and screw threads matching the screw nut 70 are provided on a part of the outer surface of the handle 20.

Embodiment 6

Figure 7:
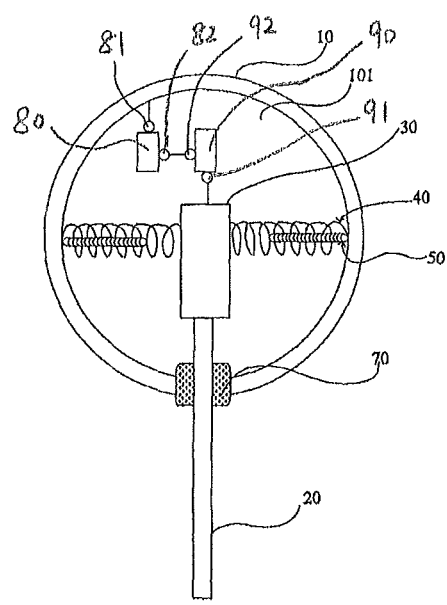
FIG. 7 is a schematic cutaway view of a structure of a tapping hammer as provided by Embodiment 6 of the present invention.

As illustrated in FIG. 7, the conductor 30 and the handle 20 may be integrally fixed together. To adjust the position of the conductor 30 in the interior hollowed-out region 101 of the hammerhead 10 along the axial direction of the conductor 30, the handle 20 may extend into the interior hollowed-out region 101 of the hammerhead 10 and be fixed to the conductor 30. The handle 20 is fixed by embedding the screw nut 70 between the hammerhead 10 and the handle 20, and the conductor 30 is fixed as well. The handle 20 is normally made of a non-conductive material. As such, in case that the handle 20 passes through the screw nut 70, it can be ensured that the conductor 30 is not electrically connected with the hammerhead 10 while no tapping force is exerted on the hammerhead 10.

Furthermore, considering the characteristics of the screw nut 70, screw threads are required to be provided on a part of the outer surface of the handle 20 to match the screw nut 70, thereby securing the conductor 30 and the handle 20.

In case that it needs to adjust the tapping force for triggering the alarm to raise an alarm, that is, to adjust the position of the conductor 30 in the interior hollowed-out region 101 of the hammerhead 10, the conductor 30 can be moved along its axial direction by rotating the handle 20.

Optionally, to further secure the handle 20 and the conductor 30 such that the conductor 30 will not be moved while the tapping hammer 1 is being tapped, at least one threaded hole may be provided on the screw nut 70. After adjusting the position of the conductor 30 in the interior hollowed-out region 101 of the hammerhead 10, a bolt matching the threaded hole provided on the screw nut 70 is screwed into the threaded hole, and the tip of the bolt abuts against a portion passing through the screw nut 70. As such, the handle 20 and the conductor 30 may be secured tightly, wherein, the portion passing through the screw nut 70 may be the conductor 30 or the handle 20, which will not be limited here. In case that it needs to adjust the position of the conductor 30 in the interior hollowed-out region 101 of the hammerhead 10, the bolt is screwed out.

In the embodiment of the present invention, the hammerhead 10 is preferably a hollow sphere. On one hand, considering the characteristics of the sphere, any part of its surface may be considered as the stress surface, and on the other hand, considering the weight of the tapping hammer 1, the tapping hammer 1 with a hollow structure has a lighter weight, which facilitates use by a user.

Furthermore, considering that the position of the conductor 30 in the interior hollowed-out region 101 of the hammerhead 10 may be adjusted by way of rotation, in the embodiment of the present invention, the conductor 30 is preferably made into a cylinder, a truncated cone or a cone.

Embodiment 7

Figure 8:
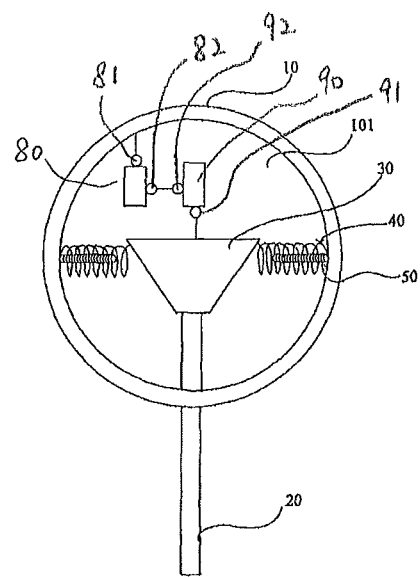
FIG. 8 is a schematic cutaway view of a structure of a tapping hammer as provided by Embodiment 7 of the present invention.

In case that the conductor 30 is a truncated cone, as illustrated in FIG. 8, considering that a plurality of first springs 40 may be provided in the tapping hammer 1, here, one end of the first spring 40 is provided at a position of the lateral surface of the conductor 30 close to the base having a larger area, and the base of the conductor 30 with a smaller area is fixedly connected to the handle 20, wherein a plane where the first spring 40 is located is a plane comprising the sphere center (that is, the sphere center of the hammerhead 10).

It should be noted that in case that the hammerhead 10 is made into a hollow structure, its thickness may be determined according to practical requirements and will not be limited here. The size of the conductor 30 may be determined according to practical requirements and will not be defined here.

Further, the at least one first spring 40 can be six first springs 40, and an angle between any two adjacent first springs 40 is 60 degrees, that is to say, there are six second springs 50 as well and an angle between any two adjacent second springs 50 is 60 degrees.

In addition, considering the characteristics of the sphere, its stress surfaces are not fixed. Therefore the six first springs 40 are evenly distributed on a plane perpendicular to the axis of the conductor 30, with the angle between any two adjacent first springs 40 as 60 degrees. Here, in the embodiment of the present invention, the plane where the first springs 40 are located is preferably a plane comprising the sphere center (that is the sphere center of the hammerhead 10).

Of course, more than six first springs 40, which are evenly distributed on the plane perpendicular to the axis of the conductor 30, can also be used.

Optionally, the tapping hammer 1 further comprises an insulating cover surrounding the hammerhead 10.

By providing the insulating cover surrounding the hammerhead 10, on one hand, the conductor (such as a conductive metal) is prevented from carrying charges due to contact with the hammerhead 10, and on the other hand, pressure may be damped while the hammerhead 10 is being tapped.

Further, the insulating cover is made of an antistatic material.

In case that the tapping hammer 1 is used in a tapping test for LCD products, an insulating cover made of an antistatic material can avoid contaminating the display products.

Based on the above tapping hammers 1, optionally, the power source may be provided inside the handle 20, and the hammerhead 10 is connected to the anode of the power source via a wire. To hear the warning from the alarm clearly, the alarm may be provided between the insulating cover and an outer surface corresponding to non-stress surface of the hammerhead 10, wherein the hammerhead 10 is not electrically connected to the alarm while no tapping force is exerted thereon. The cathode of the alarm is connected to the cathode of the power source via a wire, and the anode of the alarm is connected to the conductor 30 via a wire. The power source and the alarm may be set according to practical requirements, which will not be elaborated here.

The present invention can help the user to accurately control the tapping force for products with different tapping test requirements to reduce damage rate of products during tapping test. Furthermore, the insulating cover made of antistatic material is provided on the outer surface of the hammerhead, which may avoid contamination to display products during the tapping test on the display products.

The above disclosures are only some specific embodiments of the present invention, and the protection scope of the present invention is not limited thereto. Technical feature(s) described above may be omitted in some embodiments of the present invention to only solve part of the problems in the prior art. Moreover, the disclosed technical features may be combined in anyway. Various modifications and replacements that can be easily thought of by the person skilled in the art within the disclosed technical scope are covered by the protection scope of the present invention. The protection scope of the present invention is defined by the appended claims.

The invention claimed is:

1. A tapping hammer for tapping test, comprising a hammerhead and a handle supporting the hammerhead, the tapping hammer further comprises an alarm, a power source and a conductor, wherein,
   a hollowed-out region is provided in interior of the hammerhead and the hammerhead is elastically deformable, the hammerhead is electrically connected to a first electrode of the power source;
   the conductor is fixed in the interior hollowed-out region of the hammerhead, the conductor is not electrically connected to the hammerhead while no tapping force is exerted on the hammerhead, and the conductor is electrically connected to the hammerhead while a tapping force larger than a certain amount is exerted on the hammerhead; and
   a first electrode of the alarm is connected to the conductor, a second electrode of the alarm is connected to a second electrode of the power source.

2. The tapping hammer of claim 1, wherein the conductor is fixed to a non-stress surface of the hammerhead.

3. The tapping hammer of claim 1, wherein a distance between the conductor and an inner surface of the hammerhead is adjustable.

4. The tapping hammer of claim 1, wherein the hammer further comprises at least one first spring and at least one second spring;
   both ends of each of the at least one first spring are connected to the conductor and the inner surface of the hammerhead, respectively, and the first spring is non-conductive;
   both ends of each of the at least one second spring are fixed to a same first spring, and one end of each of the at least second spring is electrically connected to the conductor or the hammerhead;
   wherein, in case that one end of the second spring is electrically connected to the conductor, the other end of the second spring is not electrically connected to the hammerhead while no tapping force is exerted on the hammerhead, and the other end of the second spring is electrically connected to the hammerhead while a tapping force larger than the certain amount is exerted on the hammerhead; and
   in case that one end of the second spring is electrically connected to the hammerhead, the other end of the second spring is not electrically connected to the conductor while no tapping force is exerted on the hammerhead, and the other end of the second spring is electrically connected to the conductor while a tapping force larger than the certain amount is exerted on the hammerhead.

5. The tapping hammer of claim 4, wherein a length of the second spring is adjustable.

6. The tapping hammer of claim 4, wherein the hammerhead is a hollow sphere.

7. The tapping hammer of claim 6, wherein the hammer comprises a plurality of first springs, and the plurality of first springs are evenly provided on a plane perpendicular to the handle and comprising center of the sphere.

8. The tapping hammer of claim 7, wherein the hammer comprises six first springs and an angle between any two adjacent first springs is 60 degrees.

9. The tapping hammer of claim 6, wherein the conductor is coaxially provided with the handle and a position of the conductor in the interior hollowed-out region of the hammerhead is adjustable in an axis direction of the handle.

10. The tapping hammer of claim 9, wherein a guide rail is provided on a surface of the conductor, one end of the first spring is fixed in the guide rail of the conductor and is slidable along the guide rail, the other end of the first spring is fixed on the inner surface of the hammerhead, wherein an extending direction of the guide rail is perpendicular to the axis of the handle.

11. The tapping hammer of claim 9, wherein the conductor is a cylinder, a truncated cone, or a cone.

12. The tapping hammer of claim 9, wherein the tapping hammer further comprises a screw nut, wherein,
   the conductor passes through the hammerhead and extends out of the hammerhead, and is fixed to the handle;
   the screw nut is embedded between the hammerhead and the conductor, and the conductor passes through the screw nut;
   screw threads matching the screw nut are provided on a part of the outer surface of the conductor; and
   the screw nut is made of a non-conductive material.

13. The tapping hammer of claim 12, wherein a threaded hole is provided on the screw nut for securing a portion passing through the screw nut with a bolt matching the threaded hole.

14. The tapping hammer of claim 9, wherein the hammer further comprises a screw nut, wherein, the handle passes through the hammerhead and extends into the interior hollowed-out region of the hammerhead, and is fixed to the conductor;

the screw nut is embedded between the hammerhead and the handle, and the handle passes through the screw nut;

screw threads matching the screw nut are provided on a part of the outer surface of the handle.

15. The tapping hammer of claim 14, wherein a threaded hole is provided on the screw nut for securing a portion passing through the screw nut with a bolt matching the threaded hole.

16. The tapping hammer of claim 1, wherein the alarm is a buzzer or a pressure display.

17. The tapping hammer of claim 1, wherein the hammer further comprises an insulating cover outside the hammerhead.

18. The tapping hammer of claim 17, wherein the insulating cover is made of an antistatic material.

19. The tapping hammer of claim 17, wherein the power source is provided inside the handle, the alarm is provided between the insulating cover and an outer surface corresponding to non-stress surface of the hammerhead.

* * * * *